United States Patent [19]

Durden, Jr.

[11] 4,003,895

[45] Jan. 18, 1977

[54] 1,4-THIAZINES

[75] Inventor: John A. Durden, Jr., South Charleston, W. Va.

[73] Assignee: Union Carbide Corporation, New York, N.Y.

[22] Filed: Mar. 26, 1975

[21] Appl. No.: 562,130

Related U.S. Application Data

[63] Continuation-in-part of Ser. No. 319,532, Dec. 29, 1972, Pat. No. 3,894,150.

[52] U.S. Cl. .............................. 260/243 R; 424/246
[51] Int. Cl.$^2$ ........................................ C07D 279/12
[58] Field of Search .................... 260/243 R, 243

[56] References Cited

UNITED STATES PATENTS 3,790,566 2/1974 Bellina .............................. 260/243

FOREIGN PATENTS OR APPLICATIONS 41-20827 5/1966 Japan

*Primary Examiner*—John M. Ford
*Attorney, Agent, or Firm*—Robert C. Brown

[57] ABSTRACT

Novel tetrahydro thiazine carbamoyl oxime compounds having been found to exhibit exceptional insecticidal activity.

11 Claims, No Drawings

1,4-THIAZINES

This application is a continuation-in-part of my copending U.S. Pat. application Ser. No. 319,532 filed Dec. 29, 1972, now U.S. Pat. No. 3,894,150.

This invention relates to novel tetrahydro thiazine carbamoyloxime compositions which are useful as pesticides.

The novel compositions of this invention are the tetrahydro thiazin-3-one carbamoyloxime compounds corresponding to the following general formula:

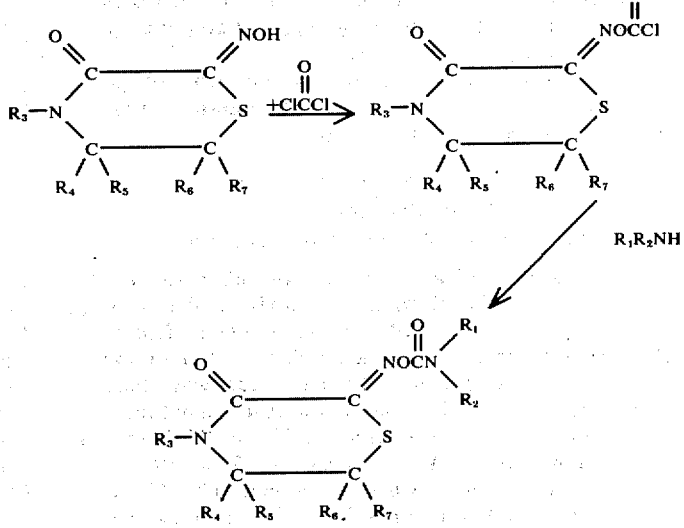

wherein $R_1$ and $R_2$ are individually, hydrogen, lower alkyl, halo-substituted lower alkyl, lower alkenyl, lower alkynyl, lower alkoxyalkyl, lower alkylthioalkyl, lower trihaloalkanesulfenyl or acyl substituents with the proviso that when $R_1$ is lower trihaloalkanesulfenyl or acyl, $R_2$ is hydrogen or lower alkyl;

$R_3$ is cycloalkyl, lower dialkylamino, lower alkoxyalkyl, lower alkylthioalkyl, heterocyclic alkyl, lower alkylcarbamoyl, carbamoyl, alkylsulfinylalkyl, alkylsulfonylalkyl or acyl;

$R_4$, $R_5$, $R_6$ and $R_7$ are individually hydrogen or lower alkyl; and $n$ is 0, 1 or 2.

These compositions, with varying degrees of efficacy are useful in combating insects, mites and nematodes. In general, the compositions having the greatest degree of activity is possessed by those compounds in which the combined total number of carbon atoms in the $R_3$, $R_4$, and $R_5$ substituents does not exceed about 8 carbon atoms.

The new compositions of this invention can be prepared conveniently in accordance with the following general reaction scheme:

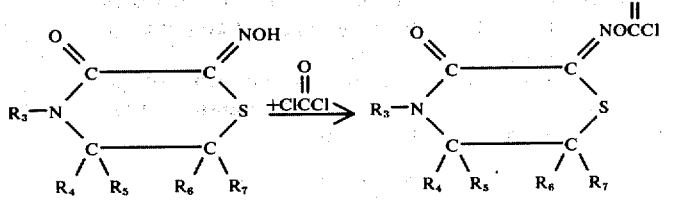

where $R_1$, $R_2$, $R_3$, $R_4$, $R_5$, $R_6$ and $R_7$ are as defined above.

The compositions of this invention where $R_1$ is hydrogen can also be prepared by reacting the appropriate oximine precursor with an isocyanate in accordance with the following general reaction scheme:

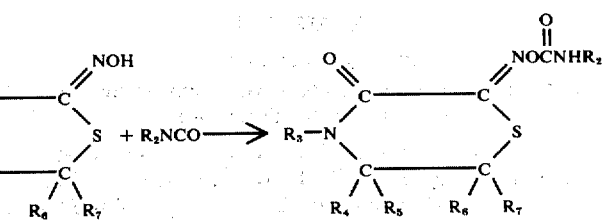

where $R_2$, $R_3$, $R_4$, $R_5$, $R_6$, and $R_7$ are as defined above.

The compositions of this invention wherein $n$ is 1 or 2 can be prepared conveniently by selective oxidation of the corresponding thiazine composition with peracetic acid.

The oxime precursor compositions are prepared conveniently, in accordance with the following general reaction scheme:

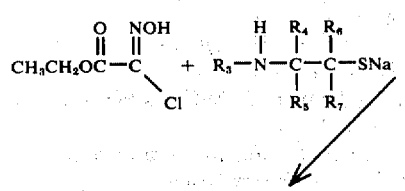

-continued

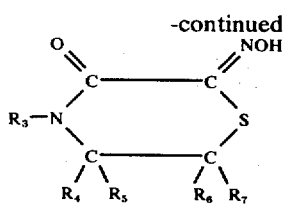

Ethoxycarbonylformhydroxamoyl chloride can be prepared from ethyl acetoacetate, as described in South African Pat. No. 69/8406 dated Dec. 27, 1968. Aminoethanethiol compositions where $R_3$ is other than hydrogen can be prepared by the method described in J. Org. Chem., 26, 5125 (1961).

The following specific examples are provided to more clearly illustrate the method of preparation of the new compositions of this invention.

EXAMPLE I

PREPARATION OF
2-Oximino-tetrahydro-1,4-thiazin-3-one

To a solution of 5.2 g. (0.13 mole) of sodium hydroxide in 150 ml of ethanol was added rapidly, under nitrogen, 15.0 g. (0.13 mole) of 2-aminoethanethiol hydrochloride with stirring and some cooling to maintain the system at room temperature. To the mixture was added a solution of 20 g. (0.13 mole) of ethoxycarbonylformhydroxamoylchloride in ethanol at 35° to 40° C with stirring and cooling. After stirring at 35° to 40° for about 30 minutes the mixture was cooled to 25° C and 200 ml of ethanol containing 5.2 g (0.13 mole) of sodium hydroxide was added with stirring over a ten minute period. After stirring over night at room temperature ethanol was removed in vacuo and the solid residue was treated with 200 ml. of water. The insoluble product was filtered, washed with water and then, isopropyl alcohol. The product was then recrystallized from water to yield, after drying, 10 g., 53 per cent of product, mp. 233°–235° C.

EXAMPLE II

PREPARATION OF
4-(Methylcarbamoyl)-2-(Methylcarbamoyloximino)-tetrahydro-1,4-Thiazin-3-one To a solution of 4 g. (0.027 mole) of the oxime of Example I in 50 ml of DMF was added 3 g. (0.053 mole) of methyl isocyanate and 3 drops of triethylamine. This mixture was left in a pressure bottle over night at room temperature after which it was added with stirring to a 50:50 ethyl ether:hexane mixture (about 200 ml.). The resulting white solid was collected, washed thoroughly with ethyl ether and air dried. Recrystallization from acetonitrile produced 4 g. (57 per cent) of product, m.p. 187°–189° C.

The following compositions in addition to those described in the above Examples are illustrative of the new compositions of this invention:

4-(2-methoxyethyl)-2-(dimethylcarbamoyloximino)-tetrahydro-1,4-thiazin-3-one,
4-acetyl-2-(N-acetyl-N-methylcarbamoyloximino)-tetrahydro-1,4-thiazin-3-one,
4-methylthioethyl-(2-methylcarbamoyloximino)-tetrahydro-1,4-thiazin-3-one,
4-(2-ethylsulfinylethyl)-2-(methylcarbamoyloximino)-tetrahydro-1,4-thiazin-3-one,
4-(isopropylsulfonylmethyl)-2-(methylcarbamoyloximino)-tetrahydro-1,4-thiazin-3-one,
4-acetyl-6-ethyl-2-(methylcarbamoyloximino)-tetrahydro-1,4-thiazin-3-one,
4-methylthioethyl-5-methyl-2-(methylcarbamoyloximino)-tetrahydro-1,4-thiazin-3-one,
4-(2-thienylmethyl)-2-[0-(methylcarbamoyl)-oximino]tetrahydro-1,4-thiazin-3-one,
4-(3-pyridylmethyl)-2-[0-(methylcarbamoyl)-oximino]tetrahydro-1,4-thiazin-3-one,
4-[2-(1,3-oxazolyl-2)ethyl]-2-[0-(methylcarbamoyl)oximino]tetrahydro-1,4-thiazin-3-one,
4-(2-tetrahydrofurylmethyl)-2-[0-(methylcarbamoyl)-oximino]tetrahydro-1,4-thiazin-3-one,
4-(1,3-dioxan-2-ylmethyl)-2-[0-(allylcarbamoyl)-oximino]tetrahydro-1,4-thiazin-3-one,
4-(1,3-oxathiolan-2-ylmethyl)-2-[0-(methylpropargylcarbamoyl)oximino]tetrahydro-1,3-thiazin-3-one,
4-(3-methyl-1,3-dithiolan-2-yl)-2-[0-(methylcarbamoyl)-oximino]tetrahydro-1,4-thiazin-3-one.
4-(2-methoxyethyl)-2-[0-(methylcarbamoyl)oximino]-tetrahydro-1,4-thiazin-3-one-1-oxide,
4-(2-methylsulfonylethyl)-2-[0-(methylcarbamoyl)-oximino]tetrahydro-1,4-thiazin-3-one-1,1-dioxide,
4-(cyclopentyl)-2-[0-(methylcarbamoyl)oximino]-tetrahydro-1,4-thiazin-3-one-1-oxide,
4-(2-norbornyl)-2-[0-(methylcarbamoyl)oximino]-tetrahydro-1,4-thiazin-3-one-1-oxide,
4-dimethylamino-2-[0-(methylcarbamoyl)oximino]-tetrahydro-1,4-thiazin-3-one,
4-propionyl-2-[0-(dimethylcarbamoyl)oximino]-tetrahydro-1,4-thiazin-3-one-1-oxide Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 per cent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 per cent by weight of compound. The test concentrations in parts per million by weight employed in the tests described hereinbelow were obtained an appropriate dilutions of the stock suspension with water. The test procedures were as follows.

Bean Aphid Foliage Spray Test

Adults and nymphal stages of the bean aphid (Aphid fabae Scop.) reared on potted dwarf nasturtium plants at 65°–70° F. and 50–70 per cent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 per cent, respectively. Aphids which fell onto the paper and were unable to remain standing after being uplighted were considered dead. Aphids remaining on the plants were observed closely for movement and those which were unable to move the length of the body upon stimulation by prodding were considered dead. Per cent mortality was recorded for various concentration levels.

Southern Armyworm Leaf Spray Test

Larvae of the southern armyworm (*Prodenia eridania*, (Cram.)), reared on Tendergreen bean plants at a temperature of 80°±5° F. and a relative humidity of 50±5 per cent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within 24 hours, no more food was added. Larvae which were unable to move the length of the body, even upon stimulation by prodding, were considered dead. Per cent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50°±5 per cent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.), reared according to the specifications of the Chemical Specialties Manufacturing Association (Blue Book, McNair-Dorland Co., N.Y. 1954; pp. 243–244, 261) under controlled conditions of 80°±5° F. and 50+5 per cent relative humidity, were the test insects. The flies were immobilized by anesthetizing with carbon dioxide and 25 immobilized individuals, males and females, were transferred to a cage consisting of a standard food strainer about 5 inches in diameter which was inverted over a wrapping-paper-covered surface. The test compounds were formulated by diluting the stock suspension with a 10 per cent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 per cent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 per cent relative humidity, were the test organisms. Infested leaves from a stock culture were placed on the primary leaves of two bean plants 6 to 8 inches in height, growing in a 2½ inch clay pot. 150–200 Mites, a sufficient number for testing, transferred from the excised leaves to the fresh plants in a period of 24 hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 per cent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and house fly was rated as follows:

1 = no control
3 = partial control

5 = excellent control
Dashes indicate no test conducted.

TABLE I

| NAME | M.P., °C. | PEST | | | | |
|---|---|---|---|---|---|---|
| | | Aphid | Mite | Southern Army-worm | Bean Beetle | Housefly |
| 4-(Methylcarbamoyl)-2-(methyl-carbamoyloximino)-tetrahydro-1,4-thiazin-3-one | 187–189 | 5 | 5 | 1 | 1 | 5 |
| 4-(2-Furylmethyl)-2-(methyl-carbamoyloximino)-tetrahydro-1,4-thiazin-3-one | 56–59 | 5 | 1 | 1 | 3 | 5 |
| 4-Cyclohexyl-2-(methylcarbamoyl-oximino)-tetrahydro-1,4-thiazin-3-one | 160–164 | 1 | 5 | 1 | 5 | 5 |
| 4-(2-Methoxyethyl)-2-[O-methyl-carbamoyl)oximino]tetrahydro-1,4-thiazin-3-one | 93–96 | 5 | 5 | 1 | 3 | 5 |

At higher dosage rates all of the above compositions may be expected to exhibit some activity against the various test species, however the data presented in Table I above clearly indicates a rather high degree of selectivity for some species and a broad spectrum of activity for others.

It will be understood that the insect species employed in the above tests are merely representative of a wide variety of pests that can be controlled by use of our compounds.

It should be noted that in addition to the insecticidal and miticidal activity indicated above, noteworthy activity against Boll Weevil was also displayed by our compounds.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 per cent by weight and in the solid formulations from about 0.5 to about 90 per cent by weight. Satisfactory sprays, dusts, or granules for general use contain from about one-fourth to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repeal the insects, they do not burn or injure the plant, and they resist weathering which includes wash-off caused by rain, decomposition by ultra-violet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

What is claimed is:

1. A compound having the structure:

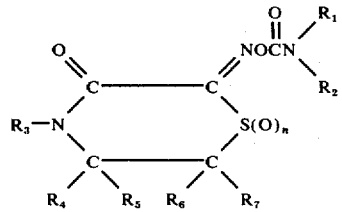

wherein:
$R_1$ and $R_2$ are individually, hydrogen, lower alkyl, halo substituted lower alkyl, lower alkenyl, lower alkynyl, lower alkoxyalkyl, lower alkyl thioalkyl, lower trihaloalkanesulfenyl or lower alkanoyl, with the proviso that when $R_1$ is lower trihaloalkanesulfenyl or lower alkanoyl, $R_2$ is hydrogen or lower alkyl;

$R_3$ is lower cycloalkyl, lower dialkylamino, lower alkoxyalkyl, lower alkylthioalkyl, lower alkylcarbamoyl, carbamoyl, alkylsulfinylalkyl, alkylsulfonylalkyl, lower furylalkyl, lower tetrahydrofurylalkyl, lower thienylalkyl, lower pyridylalkyl, lower dioxanylalkyl, lower oxazolylalkyl, lower oxathiolanylalkyl or lower dithiolanylalkyl $R_4$, $R_5$, $R_6$, and $R_7$ are individually hydrogen or lower alkyl; and $n$ is 0, 1 or 2.

2. A compound as claimed in claim 1, wherein $R_1$ is hydrogen and $R_2$ is methyl.

3. A compound as claimed in claim 1 wherein $R_1$ and $R_2$ are hydrogen, lower alkyl, lower alkanoyl or trihalomethanesulfenyl.

4. A compound as claimed in claim 1 wherein $R_1$ and $R_2$ are hydrogen or alkyl and $R_4$, $R_5$, $R_6$ and $R_7$ are hydrogen.

5. A compound as claimed in claim 1 wherein $R_1$ and $R_2$ are hydrogen, lower alkyl, lower alkyl carbamoyl or carbamoyl and $R_4$, $R_5$, $R_6$ and $R_7$ are hydrogen.

6. A compound as claimed in claim 1 wherein $R_1$ is methyl, $R_2$ is hydrogen and $R_4$, $R_5$, $R_6$ and $R_7$ are hydrogen.

7. A compound as claimed in claim 1 wherein $R_1$ is methyl, $R_2$ is hydrogen, $R_3$ is lower alkoxyalkyl having from 1 to 3 carbon atoms and $R_4$, $R_5$, $R_6$ and $R_7$ are hydrogen.

8. A compound as claimed in claim 1 wherein $n$ is 0.

9. A compound as claimed in claim 1 wherein $n$ is 1.

10. A compound as claimed in claim 1 wherein $n$ is 2.

11. 4-(2-Methoxyethyl)-2-(methylcarbamoyloximino)-tetrahydro-1,4-thiazin-3-one.

* * * * *